United States Patent [19]

Wickenhaeuser et al.

[11] Patent Number: 4,902,828
[45] Date of Patent: Feb. 20, 1990

[54] RECOVERY OF AQUEOUS GLYOXYLIC ACID SOLUTIONS

[75] Inventors: Gerhard Wickenhaeuser, Bergisch-Gladbach; Bernd Heida, Boehl-Iggelheim; Fritz Graf, Speyer; Leopold Hupfer, Friedelsheim, all of Fed. Rep. of Germany

[73] Assignee: BASF Aktiengesellschaft, Ludwigshafen, Fed. Rep. of Germany

[21] Appl. No.: 662,182

[22] Filed: Oct. 18, 1984

[30] Foreign Application Priority Data

Sep. 27, 1983 [DE] Fed. Rep. of Germany ....... 3334863

[51] Int. Cl.$^4$ ..................... C07C 51/48; C07C 59/153
[52] U.S. Cl. ..................................... 562/577; 562/513; 562/531; 562/580; 562/593; 562/608; 562/609; 568/492

[58] Field of Search ......................... 562/577, 513, 531

[56] References Cited

U.S. PATENT DOCUMENTS

| | | | |
|---|---|---|---|
| 3,281,460 | 4/1966 | Gandon et al. | 562/531 |
| 3,860,656 | 11/1975 | McCain Jr. et al. | 568/492 |
| 3,872,166 | 3/1975 | Spaezig et al. | 562/577 |
| 4,026,929 | 5/1977 | Bauer et al. | 562/577 |

Primary Examiner—Vivian Garner
Attorney, Agent, or Firm—John H. Shurtleff

[57] ABSTRACT

Aqueous glyoxylic acid solutions, essentially free of other acids, are recovered from aqueous solutions which still contain other acids, by a method in which the aqueous solution is mixed with an organic nitrogen compound at as high as 50° C., the phases are separated, and the glyoxylic acid is extracted from the organic phase with water, at a higher temperature.

9 Claims, No Drawings

RECOVERY OF AQUEOUS GLYOXYLIC ACID SOLUTIONS

The present invention relates to a process for the recovery of aqueous glyoxylic acid solutions, essentially free of other acids, from aqueous solutions which contain other acids in addition to glyoxylic acid.

It is known that glyoxylic acid can be prepared by oxidation of acetaldehyde or glyoxal with nitric acid (German Published application No. DAS 1,198,339), by electrochemical reduction of oxalic acid or by ozonolysis of benzene or maleic acid (U.S. Pat. No. 3,705,922). Among these methods, the oxidation of glyoxal with nitric acid is the most important method industrially. This process gives aqueous solutions of glyoxylic acid which, in addition to unreacted glyoxal, contain oxalic acid and smaller amounts of other organic acids and nitric acid.

In the oxidation of glyoxal with nitric acid, the amount of glyoxylic acid initially increases rapidly. However, above a certain glyoxylic acid concentration, the concentration of glyoxylic acid scarcely increases any further, while the concentration of oxalic acid increases slowly but steadily, until the reaction is terminated. Hence, in order to achieve very high selectivity in the reaction, it is necessary to dispense with complete conversion of the glyoxal, to separate off the glyoxylic acid, and to recycle the glyoxal to the reaction.

The presence of nitric acid in the reaction solutions which have not undergone complete reaction results in the continuous formation of oxalic acid by subsequent reaction of the glyoxylic acid. In isolating and purifying glyoxylic acid by crystallization, oxalic acid is difficult to separate off. There has therefore been no lack of attempts to develop methods for separating off oxalic acid and residual nitric acid from aqueous glyoxylic acid solutions.

According to German Published application No. DAS 1,198,339, first the nitric acid and then the oxalic acid are separated off with the aid of basic ion exchange resins. Glyoxal and the remaining impurities are then separated off by concentration of the solution and crystallization. This procedure has substantial disadvantages since, when the solid ion exchanger is employed in a batchwise procedure, the wash processes result in large amounts of dilute solutions, which have to be concentrated once again. Furthermore, in spite of the two purification steps using ion exchangers, the glyoxal has to be isolated by a technically complicated crystallization procedure in order to obtain a 50% strength glyoxylic acid of commercial quality.

According to German Pat. No. 2,501,743, aliphatic or cycloaliphatic $C_4$-$C_8$-alcohols or esters of aliphatic $C_1$-$C_6$-alcohols are used to extract the glyoxylic acid from reaction mixtures as obtained in an oxidation of glyoxal with nitric acid. In this procedure, the glyoxylic acid is separated off together with the other acids, which are removed by washing with water. The glyoxylic acid is then obtained from the remaining organic extract by evaporating the solvent. The separation operations are carried out by the method due to Craig, with the aid of a multistage batchwise vibrating apparatus which has been developed specially for analytical problems. Because of the large number of extraction operations, the substances being separated are obtained in an extremely low concentration, e.g. <1%. The process described cannot be extrapolated to an industrial scale.

U.S. Pat. No. 3,860,656 discloses that acidic impurities, such as nitric acid, or organic acids, such as glyoxylic acid, can be separated off from aqueous glyoxal solutions by countercurrent extraction with a solution of a relatively long-chain tertiary amine in an organic solvent. The acids are separated off from the amine by adding aqueous ammonia or other alkaline substances to the organic phase, so that the glyoxylic acid is finally obtained as a mixture with all of the other acids, in salt form. This method cannot be used to recover pure glyoxylic acid from aqueous glyoxylic acid solutions containing glyoxal and oxalic acid.

We have found that an aqueous glyoxylic acid solution, essentially free of other acids, can be particularly advantageously recovered from an aqueous solution which contains other acids in addition to glyoxylic acid by treating the aqueous solution with an organic nitrogen compound, if the treatment is carried out by mixing at as high as 50° C., and the glyoxylic acid is extracted from the resulting organic phase with water, at a higher temperature.

The novel process starts from aqueous glyoxylic acid solutions which are obtained by conventional methods for the preparation of glyoxylic acid and which contain residual starting compound and other acids in addition to glyoxylic acid. The application of the process to crude aqueous glyoxylic acid solutions which are obtained by the oxidation of glyoxal with nitric acid and which, in addition to the glyoxylic acid, contain glyoxal, oxalic acid, nitric acid and other organic acids, e.g. formic acid, is of particular industrial importance since the glyoxal can also be substantially isolated in this manner. Such aqueous starting solutions have, for example, the following composition:

from 50 to 90% by weight of water
from 5 to 35% by weight of glyoxylic acid,
from 1 to 30% by weight of glyoxal,
from 0.5 to 15% by weight of oxalic acid,
from 5 to 6% by weight of nitric acid and
from 0.3 to 3% by weight of other organic acids, e.g. formic acid, acetic acid and glycolic acid.

In the process according to the invention, the crude aqueous glyoxylic acid solutions are treated with an organic nitrogen compound, this treatment serving to extract the glyoxylic acid from the aqueous starting solution. Examples of organic nitrogen compounds are straight-chain or branched tertiary aliphatic amines having molecular weights higher than 200, such as trioctylamine, trinonylamine, tridecylamine, tridodecylamine or their isomers, as well as mixtures of these amines. These tertiary aliphatic amines are preferably used in the form of their solutions in a non-polar solvent. Examples of suitable non-polar organic solvents are paraffins, of more than 5 carbon atoms, such as heptane or octane, aromatics, such as xylene or toluene, and aliphatic ethers, such as ditert.-butyl ether, diisoamyl ether or ethyl n-butyl ether, as well as mixtures of these.

The solutions used contain about 10–60% by weight of the organic nitrogen compound.

Examples of other suitable organic nitrogen compounds are dialkylated acid amides which are derived from, for example, lower carboxylic acids, such as formic acid, acetic acid or propionic acid, and whose alkyl groups are of more than 3 carbon atoms, e.g. dibutylformamide, dibutylacetamide and dipentylformamide.

The treatment of the crude glyoxylic acid solution with the organic nitrogen compound is carried out by mixing the two phases at as high as 50° C., preferably from 10 to 45° C., extraction columns and multi-stage mixer-settler apparatuses being particularly useful for this purpose. The volume ratio of the glyoxylic acid solution to the amine solution or to the acid amide is advantageously kept at from 1:1 to 1:5.

After the extraction, the two phases are separated from one another. The glyoxylic acid is then selectively extracted from the organic phase containing the acids, water being used as extracting agent and the extraction being carried out at a higher temperature, for example not less than 20° C. above the temperature at which the crude glyoxylic acid solution is treated with the organic nitrogen compound, but not above 95° C. Washing with water in order to re-extract the glyoxylic acid from the organic phase is preferably carried out at from 30° to 95° C. The volume ratio of the organic phase to the water used for the extraction is advantageously kept at from 1:0.1 to 1:0.7. The aqueous phase contains the glyoxylic acid and is virtually free of other acids.

After the water wash, the organic phase which contains the other acids is regenerated in a conventional manner by treatment with alkaline agents, such as dilute sodium hydroxide solution, so that it can be recycled to the continuously operated process.

In an advantageous embodiment of the novel process, which embodiment gives particularly pure glyoxylic acid solutions, washing with water to extract the glyoxylic acid from the organic phase is carried out in two stages, the organic phase being treated in the first stage with some of the aqueous glyoxylic acid solution obtained in the second wash stage, and in the second stage with water. The bleed stream of the glyoxylic acid solution which is removed from the second wash stage for the first wash stage is about 20-70% by weight of the total stream. After the extraction procedure of the first stage, the aqueous bleed stream is once again combined with the crude glyoxylic acid solution. The second-stage water wash requires about 10-70 parts by weight of water per 100 parts by weight of the organic phase.

Surprisingly, the novel process possesses high selectivity, i.e. aqueous glyoxylic acid solutions which are virtually free of other acids are obtained. Moreover, pure aqueous glyoxylic acid solutions having glyoxylic acid concentrations of above 20% by weight can be obtained directly in this manner.

EXAMPLE 1

1 kg/hour of a crude aqueous glyoxylic acid solution consisting of 30% by weight of glyoxylic acid, 10% by weight of glyoxal, 3% by weight of oxalic acid, 1% by weight of nitric acid, 1% by weight of formic acid and 55% by weight of water and 2.4 kg/hour of a solution consisting of 40% by weight of tridodecylamine, 36% by weight of heptane and 24% by weight of toluene are passed simultaneously into a 5-stage mixer-settler having a capacity of 300 ml per stage. The two solutions are mixed at 45° C. to give 2.75 kg/hour of an organic phase which contains 11% by weight of glyoxylic acid, 1.4% by weight of glyoxal, and the oxalic acid, nitric acid and formic acid from the aqueous glyoxylic acid solution. At the same time, 0.65 kg/hour of an aqueous solution containing 1.5% by weight of glyoxylic acid and 8.9% by weight of glyoxal is obtained, and this solution can be recycled to the synthesis of glyoxylic acid.

In a 5-stage mixer-settler of the above design, 2.75 kg/hour of the organic phase obtained in the mixing procedure are washed, in a first wash stage, with 0.4 kg/hour of a 21% strength by weight aqueous glyoxylic acid solution at 70° C. This procedure gives 2.71 kg/hour of an organic phase containing 10.5% by weight of glyoxylic acid, 0.1% by weight of glyoxal, and the other acids stated above, and 0.44 kg/hour of an aqueous phase containing 22% by weight of glyoxylic acid and 8% by weight of glyoxal. This aqueous phase is once again combined with the starting solution.

In a second wash stage for extracting the glyoxylic acid, the organic phase is then mixed with water in a 5-stage mixer of the type described above. 2.71 kg/hour of the organic phase and 1 kg/hour of water are fed simultaneously to the mixer, and the extraction procedure is carried out at 70° C. 1.27 kg/hour of a 21% strength by weight aqueous glyoxylic acid solution which still contains 0.2% by weight of glyoxal and 2.45 kg/hour of an organic phase which contains 0.5% by weight of glyoxylic acid and <0.005% by weight of glyoxal and the other acids mentioned above are obtained. Some of the aqueous glyoxylic acid solution is removed as a bleed stream for the first wash stage for the organic phase, described above.

The organic phase is regenerated by treating it in a one-stage procedure in a mixer-settler with 20% strength sodium hydroxide solution, so that the aqueous effluent has a pH of from 9 to 11. After being washed with 0.5 kg/hour of fully demineralized water, once again in a one-stage mixer-settler apparatus, the organic tridodecylamine solution can be recycled to the process.

EXAMPLE 2 (comparative example)

The procedure described in Example 1 is followed, except that the second wash stage for the organic phase is carried out at 45° C., as in the case of the treatment of the crude glyoxylic acid solution with the organic solution. The result of this measure is that only an 8% strength aqueous glyoxylic acid solution is available for the first wash stage. The use of 0.52 kg/hour of this 8% strength glyoxylic acid solution gives 0.64 kg/hour of an aqueous solution containing 20% by weight of glyoxylic acid and 5.5% by weight of glyoxal and 2.58 kg/hour of an organic phase containing 8% by weight of glyoxylic acid, 0.08% by weight of glyoxal, and the other acids.

In the extraction in the second wash stage, 2.58 kg/hour of the organic phase are treated with 2.3 kg/hour of water at 45° C. 2.38 kg/hour of organic phase containing 0.4% by weight of glyoxylic acid and <0.005% by weight of glyoxal and 2.5 kg/hour of an 8% strength by weight aqueous glyoxylic acid solution containing 0.08% by weight of glyoxal are obtained.

We claim:
1. A process for the recovery of an aqueous glyoxylic acid solution, essentially free of other acids, from an aqueous solution which contains other acids in addition to glyoxylic acid by treating the aqueous solution with a solution of organic nitrogen compound dissolved in a non-polar organic solvent, said organic nitrogen compound being selected from the group consisting of a straight-chain or branched tertiary amine having a molecular weight higher than 200 and a dialkylated acid amide, wherein the treatment is carried out by mixing the solutions at a temperature up to 50° C., and the glyoxylic acid is extracted from the resulting organic phase with water, at a higher temperature.

2. A process as claimed in claim 1, wherein the extraction of the glyoxylic acid from the organic phase is carried out at a temperature which is not less than 20° C. higher than that at which the crude aqueous glyoxylic acid solution is treated with the organic nitrogen compound, but which does not exceed 95° C.

3. A process as claimed in claim 1, wherein a straight-chain or branched tertiary amine is used as the organic nitrogen compound.

4. A process as claimed in claim 1, wherein a dialkylated acid amide is used as the organic nitrogen compound.

5. A process as claimed in claim 1, wherein the extraction of the glyoxylic acid from the organic phase is carried out in two wash stages, the organic phase being treated in the first stage with some of the aqueous glyoxylic acid solution obtained in the second wash stage, and in the second stage with water.

6. A process as claimed in claim 1, wherein the nonpolar organic solvent is selected from the group consisting of paraffins of more than 5 carbon atoms, aromatic hydrocarbons, aliphatic ethers and mixtures thereof.

7. A process as claimed in claim 1, wherein the nonpolar organic solvent solution contains about 10–60% by weight of said organic nitrogen compound.

8. A process as claimed in claim 7, wherein the nonpolar organic solvent is selected from the group consisting of heptane, octane, xylene, toluene, di-tert.-butyl ether, diisoamyl ether, ethyl n-butyl ether and mixtures thereof.

9. A process as claimed in claim 1, wherein the organic nitrogen compound used is selected from the group consisting of trioctylamine, trinonylamine, tridecylamine, tridodecylamine, their isomers and mixtures of these amines.

* * * * *